United States Patent

Grundei et al.

Patent Number: 5,702,471
Date of Patent: Dec. 30, 1997

[54] FINGER JOINT

[75] Inventors: Hans Grundei, Lübeck; Jürgen Rudigier, Offenburg; Christian Weber, Hohwald, all of Germany

[73] Assignee: ESKA Medical GmbH & Co., Lübeck, Germany

[21] Appl. No.: 617,231

[22] Filed: Mar. 18, 1996

[30] Foreign Application Priority Data

Apr. 6, 1995 [DE] Germany ............... 195 12 854.0

[51] Int. Cl.$^6$ .................................. A61F 2/42
[52] U.S. Cl. .............................. 623/21; 403/115
[58] Field of Search ................ 623/21, 20, 18; 403/114–116

[56] References Cited

U.S. PATENT DOCUMENTS

| 3,196,463 | 7/1965 | Farneth ................... 403/114 X |
| 3,638,243 | 2/1972 | Campbell, Jr. et al. . |
| 3,851,979 | 12/1974 | Becker ................... 403/115 X |
| 4,064,568 | 12/1977 | Grundei et al. ............ 623/20 |
| 4,276,660 | 7/1981 | Laure . |
| 4,304,011 | 12/1981 | Whelan . |
| 5,147,386 | 9/1992 | Carignan et al. . |

FOREIGN PATENT DOCUMENTS

| 2 651 119 | 3/1991 | France . |
| 21 46 253 | 3/1973 | Germany . |
| 25 22 377 A1 | 11/1976 | Germany . |
| 3433263 | 3/1986 | Germany ............ 623/20 |
| 195 12 854 C1 | 8/1996 | Germany . |
| 7311107 | 1/1975 | Netherlands ............ 623/18 |
| 1567200 | 5/1990 | U.S.S.R. ............ 623/20 |

*Primary Examiner*—David H. Willse
*Attorney, Agent, or Firm*—Panitch Schwarze Jacobs & Nadel, P.C.

[57] ABSTRACT

A finger joint has first and second hollow anchorage shafts (2, 3) which can be implanted in finger tubular bones with a hinge joint (4) arranged between them. The first hollow shaft (2) can be connected with a ball cage (5) of the hinge joint (4) in which a spherical part (6) is mounted, on which a protruding stem (7) is formed. This stem (7) passes through the ball cage (5), and indeed through a slit (8) provided therefor in the wall of the ball cage (5). The slit (8) in the ball cage (5) widens continuously from the point (P) at which the stem (7) passes through the ball cage (5) in the extended position of the joint (4) to the point (M) at which the stem (7) passes through the ball cage (5) in the flexed position of the joint. In this manner, additional play is allowed to the joint in the flexed position, which largely corresponds to the physiological coordinated movement of a finger joint.

8 Claims, 2 Drawing Sheets

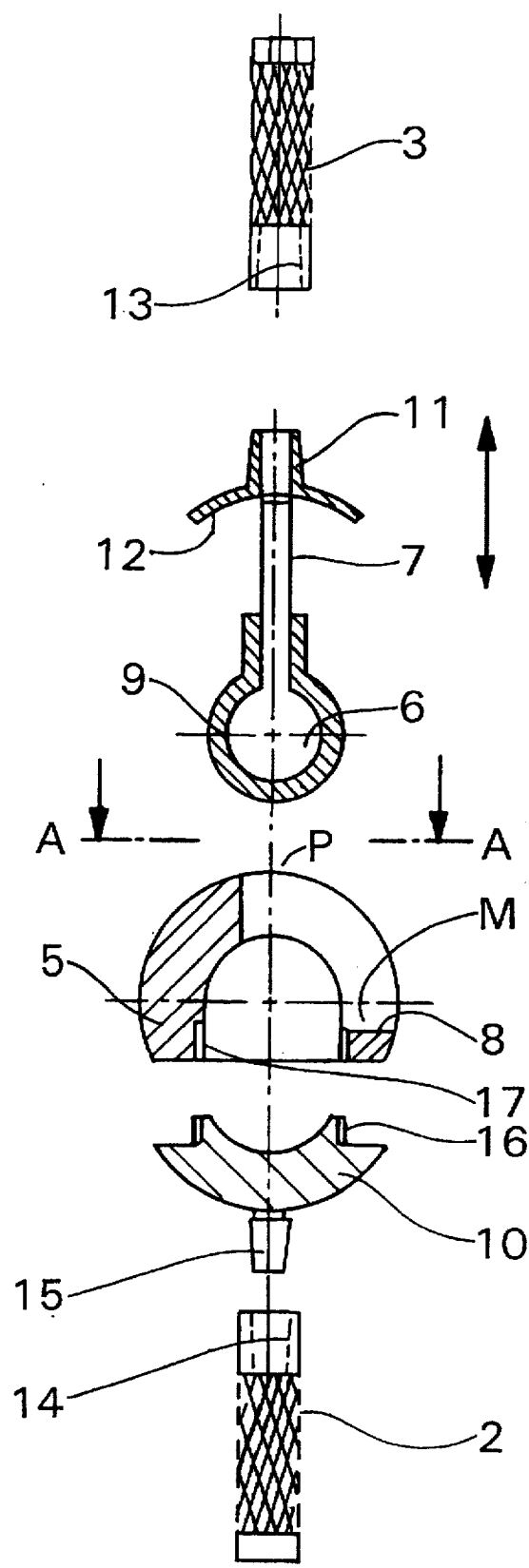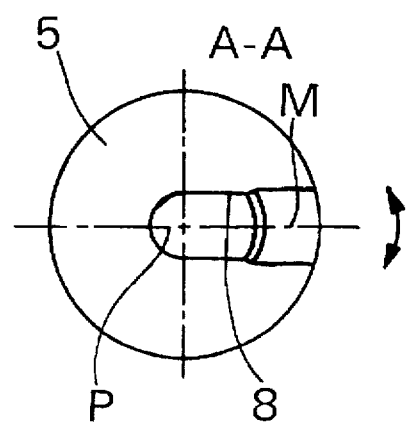
Fig. 1
Fig. 1a

FINGER JOINT

FIELD OF THE INVENTION

The invention concerns a prosthetic finger joint. It can be implanted following resection of a metacarpophalangeal joint between the bones of the hand and the finger bones, as well as of an intraphalangeal joint between the finger bones.

1. Background Of The Invention

In most cases, finger joints are resected when they are rheumatic and cause the patient great pain. Hitherto a so-called Swanson joint has been substituted for the natural joint, in connection with which, however, it is not a question of a genuine joint, but rather of a silicone substitute with two elongated anchors capable of being implanted into the tubular bones and which are connected with a foundation of silicone. The flexibility of silicone offers the patient a certain mobility of the finger treated. However, the formation of a connective tissue capsule around this "joint" has been observed, with the use of the Swanson joint, which is detrimental for the mobility and the permanency of the Swanson joint remaining in situ.

2. Summary Of The Invention

Against this background, it is an object of the present invention to create an endoprosthetic finger joint which achieves a great exactitude in imitating the natural physiological movement of a natural finger joint. In addition to this, the preconditions for the greatest wearing comfort possible for the patient should be created, in order to attain the widest acceptance possible.

This object is solved by a finger joint having first and second hollow anchorage shafts which can be implanted in tubular finger bones with a hinge joint between them in the form of a ball and socket joint, the first hollow shaft being connected with a ball cage (socket) of the hinge joint and a spherical part (ball) provided with a protruding stem being mounted in the ball cage. The protruding stem passes through a slit in the ball cage and connects with the second hollow shaft, such that the slit widens continuously from a pole point at which the protruding stem passes through the ball cage in an extended position of the joint to an equatorial point at which the protruding stem passes through the ball cage in a flexed position of the joint. Further advantageous refinements become apparent from the subclaims.

Accordingly, it is first of all proposed that the finger joint have a first and a second anchorage shaft which can be implanted in the tubular bones of the fingers or hand between which a hinge joint is arranged. The aforementioned anchorage shafts are advantageously constructed of an open-meshed grid network, preferably of metal, through which trabeculae can grow and thus assure a permanent anchorage of the shafts in the bone.

The first shaft is connected with a ball cage of the hinge joint in which is situated a spherical part provided with a stem, whereby the stem passes through the ball cage through a slit provided in it and stands in connection with a second hollow shaft. The slit in the ball cage widens from the point at which the stem passes through the ball cage in the extended position of the joint to the point at which the stem passes through the ball cage in the flexed position.

The ball and socket joint accordingly allows not only the usual bending movement of a hinge joint from the extended to the flexed position, but augments play with increasing flexion of the joint, and to be sure in the plane standing perpendicular to the plane of bending. This corresponds approximately to the coordinated movement of a natural finger joint. The significance of the most exactly recreated physiological coordinated movement lies chiefly in the fact that the soft parts surrounding the joint, such as the connective tissue and tendons, can exercise their functions in a practically unchanged environment following implantation in comparison with the natural state. Patient wearing comfort is hereby increased, and acceptance of the implant promoted by this.

The connection of the hinge joint with the two hollow shafts situated in the bones takes place preferably through conical compression connections which have been known in the area of implantation technology for a long time.

In accordance with a preferred specific embodiment, the ball cage is itself a sphere. The aforementioned slit, through which the stem of the spherical part extends, penetrates the wall of the now spherical ball cage on a section of a meridian from one pole to approximately the equator of the sphere. By constructing the ball cage in the shape of a sphere, there results a compact implant which makes possible the problem-free guidance of tendons, etc. over the ball surface in the implanted state of the finger joint. This leads to a sparing treatment of the soft parts and tendons of the fingers and, as a consequence of this, to a high tolerance of the implant.

In order to obtain the highest possible tolerance and, by way of example, to prevent metallosis, the inner spherical part is constructed in one piece with the above-mentioned stem and provided with a polyethylene coating, in accordance with an advantageous further development. Preferably, the entire spherical part is coated with polyethylene. Above and beyond this, it is likewise advantageous to coat the aforementioned stem in the projection area at the spherical part with polyethylene in the region in which it passes through the wall of the ball cage. A metal-metal contact is consequently effectively avoided if the implant is made of metal.

In case, despite all precautions, it should nonetheless become necessary to perform a revision intervention so that the spherical part may be exchanged, a pole cap of at least the size (diameter) of the spherical part is provided, which can be screwed onto the ball cage in the manner of a cover, and whose external spherical configuration completes the sphere, according to an advantageous further development. The very compact unit may thus be taken apart by unscrewing the pole cap from the ball cage, whereupon the spherical part can then be removed with the projecting stem. A new part consisting of spherical part and stem can be installed in a simple manner, and the pole cap can be closed again.

The action of the finger joint according to the invention can be further increased. For this it should, however, be noted in advance that it involves not only exclusively a bending movement with the above-mentioned enlargement of play as with the natural finger joint. A longitudinal extension also takes place. Thus, the natural tendons are placed under more traction during bending of the natural joint than is the case in the extended position of the finger. In order to compensate for these changes in length, it is provided in accordance with an advantageous further development that the stem on the spherical part of the finger joint extends quasi-telescopically into a sliding sleeve, which can be connected with the above-mentioned second hollow shaft in such a way that the stem can slide longitudinally in the sleeve. In this way, the stem can move by sliding to compensate for the changes in length and thus provide a compensating movement.

The sliding sleeve also preferably comprises polyethylene. It can be permanently connected with the second hollow shaft through a conventional conical compression joint.

The sliding sleeve preferably has a collar at its end facing the ball cage, the collar lying on the exterior of the ball cage in the assembled state of the joint. An at least partial covering of the slit through the wall of the ball cage is hereby achieved. Of course, this can best be achieved in the case where the ball cage is also itself a sphere on the exterior. Then the collar on the sliding sleeve has a partial spherical form and can almost completely cover the slit, so that the interior of the ball cage remains largely free of physiological fluids, etc., which can damage the good bearing characteristics of the joint over a long period of time.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 1 shows all parts of the finger joint according to the invention in a non-assembled (exploded) state and partially in section, while a view into the ball cage in the direction of the arrows A—A in FIG. 1 is shown in FIG. 1a.

In the drawings, the same reference symbols refer to the same parts.

DETAILED DESCRIPTION OF PREFERRED EMBODIMENT

Figure 2:
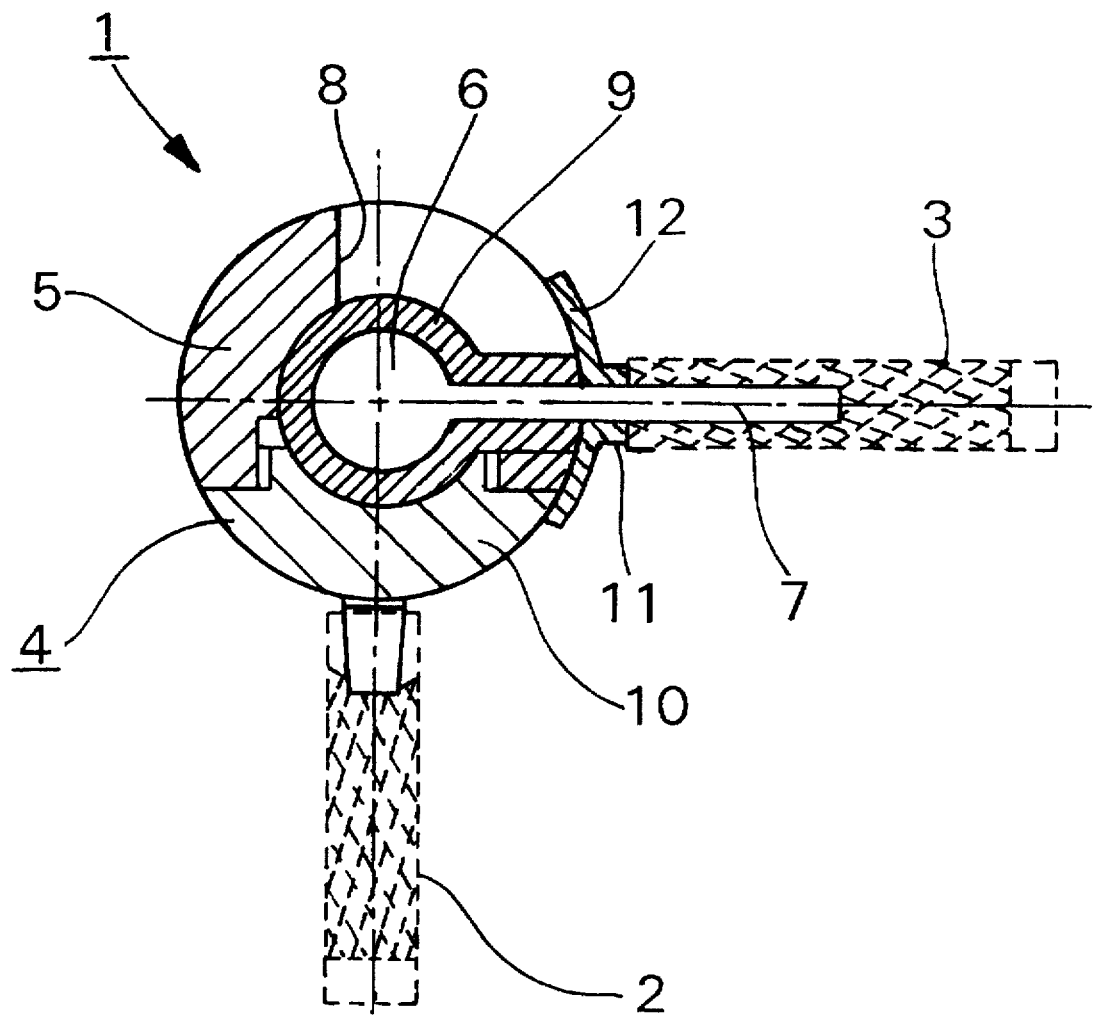
FIG. 2 is a sectional view through the assembled finger joint in the flexed position.

The ball cage 5 of the hinge joint 4 is the core piece of the finger joint 1 of the invention. In the present case, the ball cage 5 is spherically constructed and is completed in its spherical form by means of the pole cap 10. For this purpose, the thread 16 on the pole cap 10 can be screwed into the internal thread 17 of ball cage 5.

Protruding radially from the pole cap 10 is tapered cone 15 which can be connected permanently, but also separably, with a conical fitting sleeve 14 in the first hollow shaft 2 by means of a conical compression connection. In the present case, hollow shaft 2 consists of an open-meshed grid network, through which bone trabeculae of the spongiosa surrounding the shaft 2 can grow in for a permanent fixation of the implant following implantation.

The wall of the ball cage 5 is penetrated in the area from its pole P to its equator region M by a guiding slit 8. This guiding slit 8 widens continuously from the area around the pole P down to the equatorial area M of the ball cage 5, as can be clearly recognized in FIG. 1a. Through this, a greater play in the flexed position of the finger joint in the direction of the double arrow in FIG. 1a is allowed to stem 7, which is formed as an extension on the spherical part 6 (FIG. 1), than is the case with the extended finger joint, where the play is practically equal to zero. This largely corresponds to the physiological coordinated movement of a natural finger joint.

In the present case, the spherical part 6 is coated with a polyethylene layer 9 which also covers the lower region of the projecting stem 7 and, to be sure, to such an extent that no contact can take place between the (metal) stem 7 and the (metal) ball cage 5 in the area of the slit 8. A metallosis is hereby effectively prevented.

A second hollow shaft 3 is provided which, in the present case, is constructed exactly like the first hollow shaft 2, thus consisting of an open-meshed grid network and having a conical fitting sleeve 13. A sliding sleeve 11 can be brought into a conical compression connection with the conical fitting sleeve, the sliding sleeve having for this purpose the external contours of a tapered cone. The sliding sleeve 11 is, however, constructed cylindrically on the interior in such a way that the stem 7 is mounted so that it can slide longitudinally in sliding sleeve 11. In this way, a quasi-telescopic motion of the stem within sliding sleeve 11 is also made possible in the direction of the double arrow in FIG. 1 following implantation of the finger joint, by means of which longitudinally compensatory movements can be executed.

In the present case, the sliding sleeve 11 has a collar 12 on its end facing the ball cage 5 of the hinge joint 4. The ball cage 5 is here constructed in the form of a sphere, and the collar 12 lies on the outside of the ball cage 5 in the assembled state of the finger joint (FIG. 2). Here the collar 12 is to be seen as part of a spherical segment. The collar 12 serves to at least partially cover the slit 8, through which the stem 7 passes, in order to avoid a penetration by physiological fluids such as blood etc. into the interior of the ball cage. The collar 12 can be basically larger in concrete embodiments than as shown in the drawings.

The embodiment depicted permits, as is apparent from FIG. 2, a bending movement of up to 90°. The finger joint of the invention is not, however, restricted to this dimension. A bending range of 100°, for example, is also possible by lengthening the slit.

Assembly of the parts from FIG. 1 takes place in an intuitive manner by inserting the spherical part with stem 7 into the ball cage 5, after which the stem 7 protrudes through the slit 8. Thereafter the pole cap 10 is screwed onto the remaining ball cage 5. The sliding sleeve 11 is slipped over the stem 7 until the collar 12 lies on the outer wall of the ball cage. After that, the conical compression connections are made between the fitting sleeve 14 in hollow shaft 2 and the tapered cone 15 on the pole cap 10, on the one hand, and between the conical fitting sleeve 13 in hollow shaft 3 and the conical tapered cone which is formed as an extension on the exterior of the sliding sleeve 11.

It will be appreciated by those skilled in the art that changes could be made to the embodiment described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A prosthetic finger joint (1) comprising a first and a second hollow anchorage shaft (2, 3) configured to be implanted in tubular finger bones, and a hinge joint (4) in a form of a ball-and-socket joint arranged between the shafts (2,3), the first hollow shaft (2) being connected with a ball cage (5) of the hinge joint (4), a spherical part (6) provided with a protruding stem (7) being mounted in the ball cage, the stem (7) passing through a slit (8) in the ball cage (5) and connecting with the second hollow shaft (3), the slit (8) in the ball cage (5) continuously widening from a point (P) at which the stem (7) passes through the ball cage (5) in an extended position of the joint (4) to a point (M) at which the stem (7) passes through the ball cage (5) in a flexed position of the joint (4).

2. The prosthetic finger joint according to claim 1, wherein the ball cage (5) itself is a sphere, and the slit (8) penetrates through a wall of the spherical ball cage (5) on part of a meridian from a pole (P) up to approximately the equator.

3. The prosthetic finger joint according to claim 1, wherein the spherical part (6) is constructed as one piece with the stem (7) and is provided with a polyethylene coating (9).

4. The prosthetic finger joint according to claim 1, wherein a pole cap (10) of at least a diameter of the spherical part (6) is provided, whereby the pole cap (10) can be screwed onto the ball cage (5) as a cover to complete a spherical outer configuration of the ball cage (5).

5. The prosthetic finger joint according to claim 1, wherein the stem (7) extends into a sliding sleeve (11) which is connected with the second hollow shaft (3) in such a way that the stem (7) can slide lengthwise to execute longitudinal compensatory movements in the sleeve (11).

6. The prosthetic finger joint according to claim 5, wherein the sliding sleeve (11) comprises polyethylene.

7. The prosthetic finger joint according to claim 5, wherein the sliding sleeve (11) has a collar (12) on its end facing the ball cage (5), the collar (12) lying on an exterior of the ball cage in an assembled stage of the joint.

8. The prosthetic finger joint according to claim 7, wherein the collar (12) is constructed as a partial spherical segment corresponding to a spherical surface of the ball cage (5).

\* \* \* \* \*